(12) United States Patent
Kunnari

(10) Patent No.: US 9,657,047 B2
(45) Date of Patent: May 23, 2017

(54) CRYSTALLIZATION OF EPIRUBICIN HYDROCHLORIDE

(75) Inventor: Tero Kunnari, Aschaffenburg (DE)

(73) Assignee: MEDAC GESELLSCHAFT FÜR KLINISCHE SPEZIALPRÄPARATE MBH, Wedel (DE)

( * ) Notice: Subject to any disclaimer, the term of this patent is extended or adjusted under 35 U.S.C. 154(b) by 63 days.

(21) Appl. No.: 13/471,537

(22) Filed: May 15, 2012

(65) Prior Publication Data

US 2012/0309948 A1    Dec. 6, 2012

Related U.S. Application Data

(60) Provisional application No. 61/493,034, filed on Jun. 3, 2011.

(30) Foreign Application Priority Data

May 31, 2011    (DE) ........................ 10 2011 103 751

(51) Int. Cl.
*C07H 15/252*    (2006.01)
*C07H 1/06*    (2006.01)

(52) U.S. Cl.
CPC .............. *C07H 15/252* (2013.01); *C07H 1/06* (2013.01)

(58) Field of Classification Search
CPC ...................................... C07H 15/24
USPC ........................................... 536/6.4
See application file for complete search history.

(56) References Cited

U.S. PATENT DOCUMENTS

| | | |
|---|---|---|
| 4,112,076 A | 9/1978 | Arcamone et al. |
| 4,345,068 A | 8/1982 | Suarato et al. |
| 5,091,373 A | 2/1992 | Gatti et al. |
| 5,874,550 A | 2/1999 | van der Rijst et al. |
| 6,376,469 B1 | 4/2002 | Shimago et al. |
| 6,747,012 B1 * | 6/2004 | Johdo et al. ................ 514/34 |
| 7,485,707 B2 | 2/2009 | Matvienko et al. |
| 2009/0318516 A1 | 12/2009 | Burgoon et al. |

FOREIGN PATENT DOCUMENTS

| | | | |
|---|---|---|---|
| CN | 1871249 A | 11/2006 | |
| EP | 1036797 A1 | 9/2000 | |
| EP | 1 990 405 A1 | 11/2008 | |
| TW | 201004943 A | 2/2010 | |
| TW | 201143777 A | 12/2011 | |
| WO | 2008135195 A1 | 11/2008 | |
| WO | 2010/039159 A1 | 4/2010 | |
| WO | WO 2011/029576 A1 * | 3/2011 | ............. C07H 15/24 |
| WO | 2011/118929 A2 | 9/2011 | |

OTHER PUBLICATIONS

Office Action Issued Jan. 18, 2012 in German Appln. Ser. No. 10 2011 103 751.2.
Observations by a third party against EP Pat. No. 12735774.7, dated Jan. 3, 2014.
Office Action and Search Report issued Sep. 11, 2013 in TW Application No. 101119194.
Int'l Search Report and Written Opinion issued Sep. 17, 2012 in Int'l Application No. PCT/EP2012/002248.
Office Action and Search Report issued May 30, 2014 in Taiwanese Application Serial No. 101119194.
Observations by Third Parties issued May 9, 2016 in EP Application No. 13002444.1.
Arcamone et al., "Synthesis and Antitumor Properties of New Glycosides of Daunomycinone and Adriamycinone", Journ. of Medicinal Chemistry, vol. 18, No. 7, pp. 703-707 (1975).
Slawinski, et al., "The Method of Daunorubicin Purification", Acta Polonine Pharm., vol. 58, No. 4, pp. 263-268 (2001).

\* cited by examiner

*Primary Examiner* — Shaojia Anna Jiang
*Assistant Examiner* — Bahar Craigo
(74) *Attorney, Agent, or Firm* — Panitch Schwarze Belisario & Nadel LLP

(57) ABSTRACT

A crystalline epirubicin hydrochloride and a method for its production are provided. The method for producing the crystalline epirubicin hydrochloride includes the steps: (a) providing epirubicin hydrochloride, (b) producing a mixture containing the provided epirubicin hydrochloride and at least one alcohol selected from the group 1-butanol, 2-butanol, and 1-pentanol, and (c) crystallizing epirubicin hydrochloride from this mixture.

12 Claims, 2 Drawing Sheets

CRYSTALLIZATION OF EPIRUBICIN HYDROCHLORIDE

CROSS-REFERENCE TO RELATED APPLICATIONS

Applicant hereby claims the benefit of U.S. provisional patent application No. 61/493,034, filed Jun. 3, 2011, the disclosure of which is incorporated herein by reference.

BACKGROUND OF THE INVENTION

The present invention relates to crystalline epirubicin hydrochloride and to a method for its production.

Epirubicin and its acid addition salts, such as epirubicin hydrochloride, are compounds from a group of anthracyclines, which have been used since the 1980s as cytostatics for treatment of various types of solid tumors. The structure of epirubicin hydrochloride can be represented by the following formula:

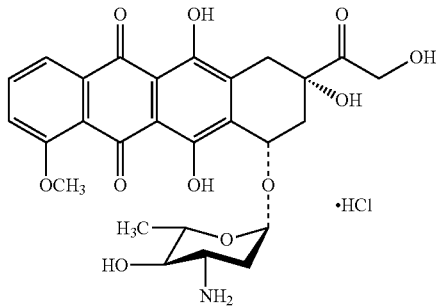

The use of epirubicin for treatment of tumors is the subject of U.S. Pat. No. 5,091,373, for example.

The production of epirubicin is described in U.S. Pat. Nos. 4,112,076 and 5,874,550, among others. For example, epirubicin and its acid addition salts can be synthesized chemically starting from daunorubicin. The production of epirubicin by the fermentation of microorganisms, however, is also possible and disclosed, for example, in European patent application Publication No. EP 1 990 405. Organic and inorganic contaminants typically accumulate during the production of epirubicin, and their proportion can be up to 25 weight percent of the produced product mixture. For this reason, purification of epirubicin or its corresponding acid addition salts after production is essential.

A suitable method for purifying epirubicin hydrochloride emerges from U.S. Pat. No. 4,861,870. Here, epirubicin hydrochloride is precipitated from an aqueous solution with the help of acetone and is obtained as an amorphous solid. With this method it is possible to obtain amorphous epirubicin hydrochloride in largely pure form.

In U.S. Pat. No. 7,485,707 and International patent application Publication No. WO 2010/039159 there are described certain crystalline forms of epirubicin hydrochloride, which are characterized by different x-ray diffraction patterns, that exhibit improved thermal stability compared with known modifications of epirubicin hydrochloride. These crystalline modifications should be able to be obtained by precipitating epirubicin hydrochloride from a solution or a gel by adding hydrophilic organic solvent. With the post-processing of the method described in these patent documents, however, it was determined that crystalline epirubicin hydrochloride cannot be obtained with the described x-ray diffraction patterns under the specified conditions.

Furthermore, the problem is known from the prior art that the production or crystallization of epirubicin hydrochloride leads to an undesired formation of dimers and decomposition products, such as doxorubicinone.

Therefore, there is also a need for a thermally stable modification of crystalline epirubicin hydrochloride and a simple and reliable method for producing such a thermally stable modification of crystalline epirubicin hydrochloride in high purity.

BRIEF SUMMARY OF THE INVENTION

The invention is therefore based on the object of providing a thermally stable modification of crystalline epirubicin hydrochloride.

The invention is further based on the object of providing a simple and reliable method for producing such a thermally stable modification of crystalline epirubicin hydrochloride in high purity.

The invention therefore provides a method for producing crystalline epirubicin hydrochloride, comprising the steps:
  (a) providing of epirubicin hydrochloride;
  (b) producing a mixture containing the provided epirubicin hydrochloride and at least one alcohol selected from the group consisting of 1-butanol, 2-butanol, and 1-pentanol; and
  (c) crystallizing epirubicin hydrochloride from this mixture.

The invention also provides crystalline epirubicin hydrochloride obtained by this method.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

DETAILED DESCRIPTION OF THE INVENTION

According to the invention, crystalline epirubicin hydrochloride is produced.

This crystalline epirubicin hydrochloride preferably has a peak in a Differential Scanning calorimetry (DSC) diagram having a maximum intensity in the temperature range of 195-205° C., more preferably having a maximum intensity in a temperature range of 198-202° C., and in particular having a maximum intensity at a temperature of 200° C. This peak preferably involves an exothermic peak.

According to another preferred embodiment, crystalline epirubicin hydrochloride of the invention has an additional peak in the Differential Scanning calorimetry (DSC) diagram having a maximum intensity in the temperature range of 240-260° C. and in particular having a maximum intensity in the temperature range of 245-255° C. This additional peak preferably involves an endothermic peak.

The Differential Scanning calorimetry (DSC) diagram can be obtained within the scope of the invention, for example, by heating a sample of crystalline epirubicin hydrochloride (for example corresponding to a quantity of 1-8 mg epirubicin hydrochloride) to 30-350° C. at a heating rate of 10-20° K/min, preferably 10° K/min, in a DSC calorimeter.

Figure 1:
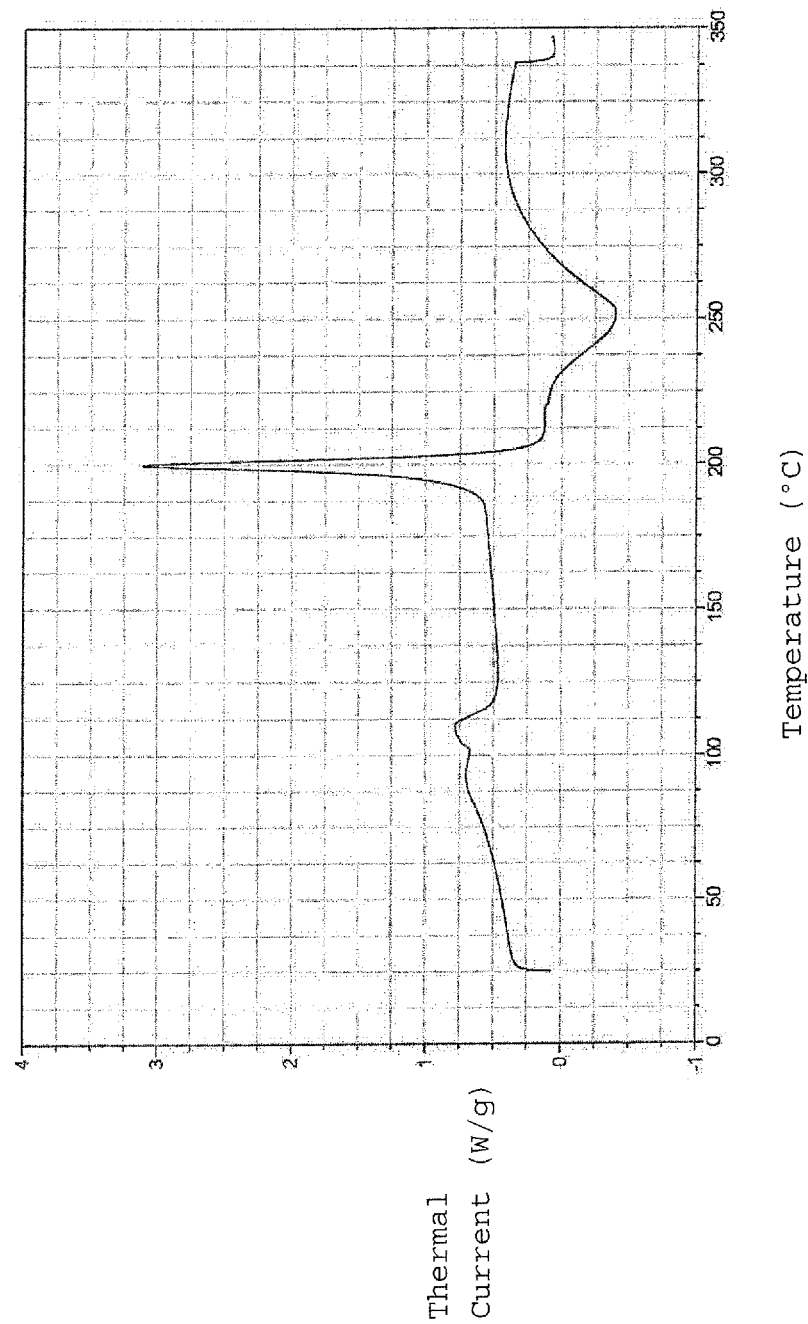
FIG. 1 is a typical DSC diagram of crystalline epirubicin hydrochloride produced according to an embodiment of the invention.

A typical DSC diagram of crystalline epirubicin hydrochloride according to an embodiment of the invention is shown in FIG. 1.

Crystalline epirubicin hydrochloride of the invention is preferably characterized at least by peaks in a powder x-ray diffraction diagram at average values for the diffraction angle (2Θ) in the following ranges: 5.04-5.14, 9.00-9.20, 13.50-13.80, 22.00-22.20, 22.40-22.50, 22.51-22.60, 23.90-24.10, and 25.70-25.90.

According to one preferred embodiment, the crystalline epirubicin hydrochloride has at least peaks at the following average values for the diffraction angle (2Θ) in a powder x-ray diffraction diagram: 5.09, 9.10, 13.63, 22.10, 22.46, 22.52, 24.00, and 25.77.

According to one especially preferred embodiment, crystalline epirubicin hydrochloride is characterized by a powder x-ray diffraction pattern having relative intensities P (%) at average values for the diffraction angle (2Θ) according to the following table:

| Diffraction angle (2Θ) | Relative intensity P(%) | Preferred relative intensity P(%) |
|---|---|---|
| 5.09 | 100-80 | 100 |
| 9.10 | 80-60 | 71 |
| 13.63 | 100-80 | 98 |
| 22.10 | 55-45 | 50 |
| 22.46 | 95-75 | 85 |
| 22.52 | 100-80 | 100 |
| 24.00 | 100-80 | 100 |
| 25.77 | 65-50 | 56 |

According to another preferred embodiment, crystalline epirubicin hydrochloride is characterized preferably at least by peaks at the following average values for the diffraction angle (2Θ) in a powder x-ray diffraction diagram: 5.09, 9.10, 9.47, 11.51, 12.01, 12.34, 13.62, 14.59, 16.11, 16.37, 16.50, 18.02, 19.11, 19.36, 20.82, 21.02, 21.37, 22.10, 22.46, 22.52, 23.29, 24.00, 25.77, 27.67, and 29.69.

According to another especially preferred embodiment, crystalline epirubicin hydrochloride is characterized by a powder x-ray diffraction pattern having relative intensities P (%) at average values for the diffraction angle (2Θ) according to the following table, wherein only relative intensities P≥10% are specified:

| Diffraction angle (2Θ) | Relative intensity P(%) | Preferred relative intensity P(%) |
|---|---|---|
| 5.09 | 100-80 | 100 |
| 9.10 | 80-60 | 71 |
| 9.47 | 15-10 | 13 |
| 11.51 | 25-18 | 22 |
| 12.02 | 22-14 | 18 |
| 12.34 | 30-20 | 26 |
| 13.63 | 100-80 | 98 |
| 14.59 | 60-40 | 49 |
| 16.11 | 40-30 | 34 |
| 16.50 | 45-33 | 37 |
| 18.02 | 30-20 | 24 |
| 19.11 | 25-15 | 21 |
| 19.36 | 35-25 | 29 |
| 20.82 | 25-15 | 20 |
| 21.02 | 33-20 | 27 |
| 21.37 | 40-50 | 46 |
| 22.10 | 55-45 | 50 |
| 22.46 | 95-75 | 85 |
| 22.52 | 100-80 | 100 |
| 24.00 | 100-80 | 100 |
| 25.77 | 65-50 | 56 |
| 27.67 | 55-40 | 47 |
| 29.69 | 25-40 | 32 |

According to the invention, it can be preferred that the term "peak" is understood to be the signal of this peak having the maximum intensity.

Figure 2:
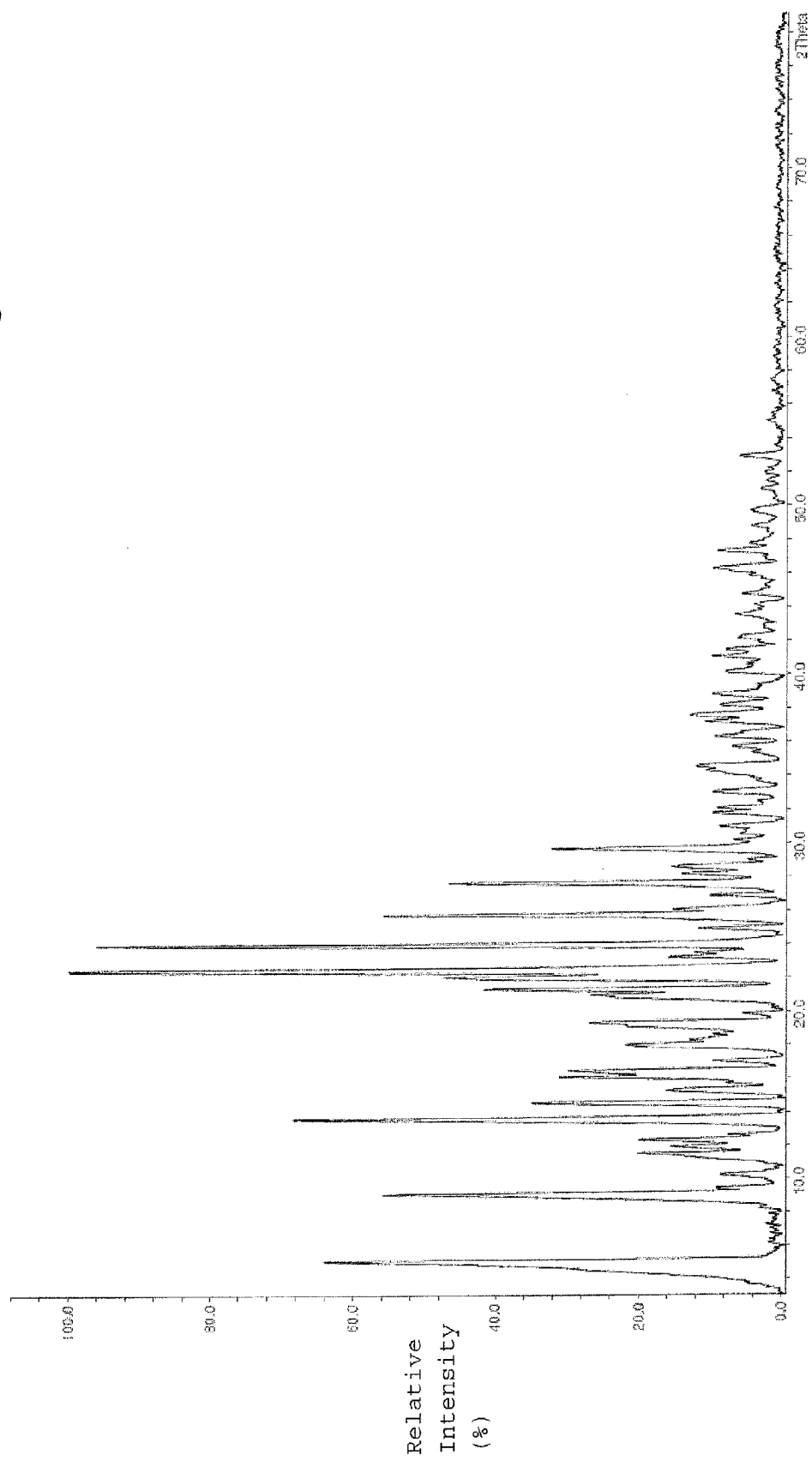
FIG. 2 is a typical powder x-ray diffraction diagram of crystalline epirubicin hydrochloride produced according to an embodiment of the invention.

A typical powder x-ray diffraction diagram of crystalline epirubicin hydrochloride produced according to an embodiment of the invention is shown in FIG. 2.

The above values relate to x-ray diffraction measurements measured with a powder x-ray diffractometer made by the company Stoe (Darmstadt) by an IPPSD detector (image plate position-sensitive detector) using Cu—Kα radiation (λ=1.5406 Å) (Ge monochromator). The measurement range for 2Θ was 3 to 79. The measurement devices were calibrated against Si 5N=99.999%. The accuracy of the obtained values equals 1.0%.

For producing crystalline epirubicin hydrochloride, initially epirubicin hydrochloride is provided in a step (a). This epirubicin hydrochloride can be produced in a known manner, for example using fermentation or chemical synthesis.

The provision of epirubicin hydrochloride can take place as a solid, in a suspension, or in a solution. Preferably, epirubicin hydrochloride is provided in solid form or in a solution.

If epirubicin hydrochloride is provided as a solid, this can be present as amorphous epirubicin hydrochloride or as crystalline epirubicin hydrochloride.

If epirubicin hydrochloride is provided in a solution, then it preferably involves an aqueous solution of epirubicin hydrochloride. According to one especially preferred embodiment, this aqueous solution is a concentrated aqueous solution of epirubicin hydrochloride. By aqueous solution of epirubicin hydrochloride is understood, according to the invention, a solution containing epirubicin hydrochloride and water. The percentage of water in this solution is preferably in the range of 30-70 volume percent and more preferably in the range of 40-60 volume percent, relative to the total volume of aqueous solution containing epirubicin hydrochloride.

In addition to epirubicin hydrochloride and water, the aqueous solution can however optionally also contain additional components, in particular at least one additional solvent. This at least one additional solvent can involve, for example, an alcohol. Here, as alcohols, ethanol, 1-propanol, 2-propanol, or mixtures thereof are preferred. The proportion of the at least one alcohol preferably lies in the range of 30-70 volume percent and more preferably in the range of 40-60 volume percent, relative to the total volume of the aqueous solution containing epirubicin hydrochloride. The content of epirubicin hydrochloride in this aqueous solution equals preferably 100-400 g/l and more preferably 150-350 g/l, relative to the total volume of the aqueous solution containing epirubicin hydrochloride. According to one preferred embodiment, the pH value of the aqueous solution containing epirubicin hydrochloride lies in the range of 3.5-4.5.

The epirubicin hydrochloride provided in step (a) is used in a step (b) for producing a mixture. For this purpose, the provided epirubicin hydrochloride, preferably present as a solid or in a solution, is combined with at least one alcohol selected from the group consisting of 1-butanol, 2-butanol, and 1-pentanol.

Accordingly, a mixture is formed that contains at least epirubicin hydrochloride and at least one alcohol selected from the group consisting of 1-butanol, 2-butanol, and 1-pentanol. It has proven especially advantageous for the crystallization to produce a mixture that contains, in addition to epirubicin hydrochloride, at least 1-butanol.

The presence of an alcohol selected from the group consisting of 1-butanol, 2-butanol, and 1-pentanol, in particular 1-butanol, contributes surprisingly to the prevention of gel formation that is otherwise typical for epirubicin hydrochloride and that is an obstacle to crystallization of epirubicin hydrochloride. Accordingly, just the presence of at least one alcohol selected from the group consisting of 1-butanol, 2-butanol, and 1-pentanol allows the growth of epirubicin hydrochloride crystals.

According to one preferred embodiment, the proportion of the at least one alcohol selected from the group consisting of 1-butanol, 2-butanol, and 1-pentanol lies in the range of 5-100 volume percent, more preferably in the range of 5-50 volume percent, even more preferably in the range of 5-30 volume percent, especially preferred in the range of 6-20 volume percent, and very especially preferred in the range of 7-15 volume percent, relative to the total volume of the mixture in step (b). At a concentration of less than 5 volume percent of the at least one alcohol selected from the group consisting of 1-butanol, 2-butanol, and 1-pentanol, relative to the total volume of the mixture, it has been shown that the tendency toward crystallization of epirubicin hydrochloride decreases significantly.

According to another preferred embodiment, the mixture in step (b) contains, in addition to epirubicin hydrochloride and at least one alcohol selected from the group consisting of 1-butanol, 2-butanol, and 1-pentanol, at least one additional alcohol. This additional alcohol is preferably selected from the group consisting of ethanol, 1-propanol, and 2-propanol. According to one especially preferred embodiment, the additional alcohol is 2-propanol.

Preferably, the proportion of the at least one additional alcohol selected from the group consisting of ethanol, 1-propanol, and 2-propanol lies in the range of 5-95 volume percent, more preferably in the range of 10-94 volume percent, even more preferably in the range of 50-93 volume percent, especially preferred in the range of 75-92 volume percent, and very especially preferred in the range of 80-90 volume percent, relative to the total volume of the mixture.

If an additional alcohol is contained in the mixture, wherein this additional alcohol is selected from the group consisting of ethanol, 1-propanol, and 2-propanol, then it can be preferred that the ratio of the volume of this additional alcohol to the volume of the alcohol selected from the group consisting of 1-butanol, 2-butanol, and 1-pentanol lies in the range of 3:1 to 20:1, more preferably in the range of 5:1 to 15:1, and even more preferably in the range of 7:1 to 10:1.

The mixture produced in step (b) can also have other additional components. One preferred additional component can be, for example, water. Preferably, the proportion of water is below 7 volume percent, relative to the total volume of the mixture. A higher percentage of water in the mixture could reduce the yield. According to one preferred embodiment, the proportion of water is in the range of 0.5-7 volume percent and more preferably in the range of 3-5 volume percent, relative to the total volume of the mixture.

It has proven especially advantageous if, in step (b), a mixture is produced that contains, in addition to epirubicin hydrochloride, 80-90 volume percent 2-propanol, 5-15 volume percent 1-butanol, and 2-6 volume percent water, relative to the total volume of the mixture.

According to an embodiment of the invention, it can be further advantageous that the proportion of epirubicin hydrochloride lies in the range of 5-100 g/l, preferably in the range of 6-100 g/l, more preferably in the range of 10-50 g/l, and even more preferably in the range of 25-35 g/l, relative to the total volume of the mixture in step (b). A concentration of epirubicin hydrochloride in this range leads to a surprisingly high yield of crystalline epirubicin hydrochloride, which in this case can be, for example, approximately 95 weight percent.

The mixture produced in step (b) can be a solution or a suspension. A solution of epirubicin hydrochloride is typically obtained when a solution of epirubicin hydrochloride, for example an aqueous solution of epirubicin hydrochloride, is present before the addition of the at least one alcohol. In contrast, the mixture in step (b) is typically present as a suspension when epirubicin hydrochloride is present as a solid before the addition of the at least one alcohol.

A pH value of the mixture in step (b) in the range of 2.5-4.5 has proven especially advantageous for the crystallization. An optimum crystallization is obtained here if the pH value of the mixture in step (b) lies in the range of 3.0-4.5, more preferably in the range of 3.5-4.5, and in particular in the range of 3.9-4.1. If the mixture is produced by adding the at least one alcohol to epirubicin hydrochloride as a solid, then the mixture typically already has a pH value in this range. If the production of the mixture is realized by adding the at least one alcohol to a solution containing epirubicin hydrochloride, then the mixture could have a higher pH value. In this case, the pH value can be adjusted to the preferred range, for example by adding hydrochloric acid.

In step (c) the crystallization of epirubicin hydrochloride takes place. For this purpose, the mixture obtained in step (b) can be left standing, for example, until crystalline epirubicin hydrochloride forms. If necessary, the mixture can be stirred here.

The mixture can also be heated, however, for accelerating the crystallization. According to one preferred embodiment, the mixture is heated to a temperature in the range of 40-80° C., more preferably in the range of 50-75° C., and even more preferably in the range of 60-70° C. At temperatures below 40° C. the crystallization of epirubicin hydrochloride from the mixture takes place only slowly, while at temperatures above 80° C. the epirubicin hydrochloride obtained in the mixture is slowly broken down. The mixture is preferably heated while being stirred.

According to another preferred embodiment, the mixture is left at a temperature in the range specified above for a time period of at least two hours, for example for a time period in the range of 2-8 hours, 4-8 hours, or 4-6 hours. Here, the mixture can optionally also be stirred.

Then, the heated mixture can be cooled. The cooling can take place, for example, at a temperature in the range of 20-30° C., in particular at a temperature of 25° C.

It has been shown that crystalline epirubicin hydrochloride is thermodynamically more stable than amorphous epirubicin hydrochloride. With crystallization of epirubicin hydrochloride from a solution, crystalline epirubicin hydrochloride is typically obtained directly. If the crystallization of epirubicin hydrochloride is performed from a suspension containing amorphous epirubicin hydrochloride, then the amorphous epirubicin hydrochloride typically initially present in the suspension as a solid is gradually converted into the thermodynamically more stable crystalline epirubicin hydrochloride.

After the crystallization, the produced crystals can be separated from the rest of the mixture. The separation here takes place preferably by filtration or distillation.

If necessary or desired, the crystals can then be washed. The washing can take place, for example, with a ketone, for example acetone.

After the optional washing of the crystals, the crystals can in turn be separated from the washing solution. Here also, the separation typically takes place by filtration or distillation.

The isolated solid can finally be dried. The drying preferably takes place until the weight becomes constant and also preferably under a vacuum.

The invention is described below with reference to examples that should not, however, limit the scope of protection.

EXAMPLES

Example 1

9.0 g amorphous epirubicin hydrochloride was suspended in a mixture of 12 ml water, 258 ml 2-propanol, and 30 ml 1-butanol. This suspension was heated to 65° C. while stirring and left at this temperature for four hours. Here, the solid contained in the suspension was not completely dissolved, but instead was gradually converted from an amorphous modification into a crystalline modification. The suspension was cooled stepwise to a temperature of 22° C. After the removal of the solvent contained in the suspension by filtration, the crystals were washed with acetone and dried for 24 hours under vacuum after the removal of acetone.

Then, the purity of the resulting epirubicin hydrochloride was tested. The presence of dimers or decomposition products was not detected. The yield equaled 95%.

The produced crystalline epirubicin hydrochloride was subjected to a test of thermal stability. For this purpose, the produced crystals were stored at a temperature of 40° C. for a time period of one week, two weeks, and three weeks. Within this time frame, no decomposition of the crystalline epirubicin hydrochlorides could be detected. Instead, the crystals remained in unchanged form.

Example 2

10.0 g amorphous epirubicin hydrochloride was dissolved in a mixture of 13 ml water and 13 ml 2-propanol, in order to prepare a solution containing epirubicin hydrochloride. This solution was then mixed with 33 ml 1-butanol and 274 ml 2-propanol. The produced mixture was heated to 65° C. and left at this temperature for four hours, whereby epirubicin hydrochloride crystals were formed. Then, the obtained suspension was cooled stepwise to a temperature of 22° C. The solvent contained in the suspension was removed by filtration, and the crystals remaining as filter residue were washed with acetone. After removing the acetone, the crystals were dried for 24 hours under vacuum.

Then, the purity of the produced epirubicin hydrochlorides was tested. The presence of dimers or decomposition products was not detected. The yield equaled 95%.

The produced crystalline epirubicin hydrochloride was subjected to a test of thermal stability. For this purpose, the produced crystals were stored at a temperature of 40° C. for a time period of one week, two weeks, and three weeks. Within this time frame, no decomposition of the crystalline epirubicin hydrochlorides could be detected. Instead, the crystals remained in unchanged form.

Comparison Example 1

A solution of epirubicin hydrochloride (10.0 g) was produced in water (pH 3.5), and the solution was subjected to drying under vacuum at a temperature of 40° C. until a gel-like state was reached. The solution thus obtained was mixed with 300 ml acetone, in order to precipitate epirubicin hydrochloride from this solution. The precipitate produced was obtained from the solution by filtration and washed with 50 ml acetone.

Then, the purity of the obtained epirubicin hydrochloride was tested. The yield initially equaled 95%. The presence of dimers was detected.

The epirubicin hydrochloride produced was subjected to a test of thermal stability. For this purpose, the epirubicin hydrochloride was stored at a temperature of 40° C. for a time period of one week, two weeks, and three weeks. Within this time frame, a thermal decomposition of epirubicin hydrochloride amplified with increasing storage period by two percent respectively was observed.

Comparison Example 2

Example 1 of U.S. Pat. No. 7,485,707 was followed, and initially a solution of epirubicin hydrochloride (10.0 g) was produced in water (pH 3.5), which was subjected to drying under vacuum at a temperature of 40° C. until a gel-like state was reached. The solution produced was mixed with twelve times the volume of 1-propanol and stirred for three hours at a temperature of 60° C. No crystalline epirubicin hydrochloride according to the present invention was produced.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method for producing crystalline epirubicin hydrochloride, comprising steps of:
   (a) providing epirubicin hydrochloride;
   (b) combining the epirubicin hydrochloride provided in step (a), at least one first alcohol selected from the group consisting of 1-butanol, 2-butanol, and 1-pentanol, and at least one second alcohol which is 2-propanol to produce a mixture containing the epirubicin hydrochloride, the at least one first alcohol, the at least one second alcohol and water, the water being provided in step (a) and/or step (b), a proportion of the epirubicin hydrochloride contained in the mixture being in the range of 10-50 g/l relative to the total volume of the mixture; and (c) crystallizing the epirubicin hydrochloride from the mixture produced in step (b) by heating the mixture produced in step (b) to a temperature in the range of 50-75° C. for a time period of at least 2 hours.

2. The method according to claim 1, wherein the epirubicin hydrochloride provided in step (a) is contained in a solution.

3. The method according to claim 2, wherein the solution is an aqueous solution.

4. The method according to claim 3, wherein the epirubicin hydrochloride provided in step (a) is contained in a proportion of 100-400 g/l, relative to the total volume of the aqueous solution.

5. The method according to claim 1, wherein the epirubicin hydrochloride provided in step (a) is in crystalline or amorphous form.

6. The method according to claim 1, wherein the at least one first alcohol is present in the mixture produced in step (b) in a proportion lying in a range of 5-50 volume percent, relative to the total volume of the mixture.

7. The method according to claim 1, wherein the at least one second alcohol is present in the mixture produced in step (b) in a proportion lying in a range of 5-95 volume percent, relative to the total volume of the mixture.

8. The method according to claim 1, wherein the ratio of a volume of the second alcohol to a volume of the first alcohol lies in the range of 3:1 to 20:1.

9. The method according to claim 1, wherein, in step (b), the proportion of the water in the mixture lies in the range of 0.5-7 volume percent, relative to the total volume of the mixture.

10. The method according to claim 1, wherein a pH value of the mixture produced in step (b) lies in the range of 2.5-4.5.

11. The method according to claim 1, wherein in step (c) the mixture is left at a temperature in the range of 50-75° C. for a time period of 2-8 hours.

12. The method according to claim 1, wherein crystals produced in step (c) are separated from the remainder of the mixture.

* * * * *